United States Patent
Firth et al.

(10) Patent No.: US 8,222,014 B2
(45) Date of Patent: Jul. 17, 2012

(54) PLANAR ELECTROPORATION APPARATUS AND METHOD

(75) Inventors: Kevin L. Firth, Kingston (CA); Leda Raptis, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 1175 days.

(21) Appl. No.: 12/073,167

(22) Filed: Feb. 29, 2008

(65) Prior Publication Data

US 2008/0213855 A1 Sep. 4, 2008

Related U.S. Application Data

(60) Provisional application No. 60/904,188, filed on Mar. 1, 2007.

(51) Int. Cl.
| | |
|---|---|
| C12N 13/00 | (2006.01) |
| C12N 15/87 | (2006.01) |
| C12M 1/42 | (2006.01) |
| C12M 1/34 | (2006.01) |
| C12M 3/00 | (2006.01) |

(52) U.S. Cl. ............... 435/173.6; 435/285.2; 435/461; 435/288.3

(58) Field of Classification Search ................. None
See application file for complete search history.

(56) References Cited

U.S. PATENT DOCUMENTS

| | | | |
|---|---|---|---|
| 4,292,408 | A | 9/1981 | Zimmermann et al. |
| 4,622,302 | A | 11/1986 | Sowers |
| 4,832,814 | A | 5/1989 | Root |
| 5,137,817 | A | 8/1992 | Busta et al. |
| 5,232,856 | A | 8/1993 | Firth |
| 6,352,853 | B1 | 3/2002 | King et al. |
| 6,482,619 | B1 | 11/2002 | Rubinsky et al. |

FOREIGN PATENT DOCUMENTS

| | | |
|---|---|---|
| EP | 1672063 A1 | 6/2006 |
| WO | WO01/07583 A1 | 2/2001 |
| WO | WO2005/075656 A1 | 8/2005 |

OTHER PUBLICATIONS

Website document entitled: "Enasco: Petri Dishes—100 mm Diameter Divided" (available at http://www.enasco.com/product/SB45991M). Downloaded from website Oct. 4, 2011.*

Boccaccio, C., et al., Induction of epithelial tubules by growth factor HGF depends on the STAT pathway, Nature 391: 285-288 (Jan. 15, 1998).

Brownell, H.L., et al., Ras is involved in gap junction closure in proliferating fibroblasts or preadipocytes . . . adipocytes, DNA and Cell Biology 15(6): 443-451 (1996).

Ennaji, M.M., et al., Alterations in cell-cell communication in human papillomavirus type 16 . . . myoblasts, Cellular and Molecular Biology 41(4): 481-498 (1995).

Fick, J., et al., The extent of heterocellular communication mediated by gap junctions is predictive of bystander tumor cytotoxicity in vitro, PNAS USA, 92: 11071-11075 (1995).

Huang, K.-S., et al., Enhancement of an electroporation system . . . electrodes, Proc. of the 2005 IEEE, Eng. in Med. & Biology 27th Annual Conf., 522-525 (Sep. 1-4, 2005).

Huang, K.-S., et al., Enhancement of an electroporation system for gene delivery using electrophoresis with a planar electrode, Lab Chip, 7: 86-92 (2007).

Khine, M., et al., A single cell electroporation chip, The Royal Society of Chemistry, Lab Chip 5: 38-43 (2005).

Lin, Y.-C., et al., Electroporation microchips for in vitro gene transfection, J. Micromech. Microeng. 11: 542-547 (2001).

Liu, F., et al., Mechanism of in vivo DNA transport into cells by electroporation: electrophoresis across the plasma . . . involved, J. Gene Med. 8: 353-361 (2006).

Raptis, L.H., et al., A novel technique for the study of intercellular, junctional communication: Electroporation of . . . slide, DNA and Cell Biology 13(9): 963-975 (Sep. 1994).

Raptis, L.H., et al., Electroporation of adherent cells in situ for the introduction of nonpermeant molecules, Methods in Molecular Biology 48: 93-113 (1995).

Raptis, L., et al., Electroporation of adherent cells in situ for the study of signal transduction and . . . communication, Methods in Molecular Biology 423: 173-189 (2008).

Raptis, L., et al., Dissecting pathways; in situ electroporation for the study . . . communication, Cell Biology, a Handbook, Elsevier Science, Cambridge, Chapter 44 (2005).

Wood, K.C., et al., Electroactive controlled release thin films, PNAS 105(7): 2280-2285 (2008).

Yaoita et al., Potential-controlled morphological change and lysis of heLa cells cultured on an electrode surface, Biochemistry and Bioenergetics 20: 169-177 (1988).

International Search Report and Written Opinion of the International Searching Authority for corresponding PCT/CA2008/000406, filed Feb. 29, 2008.

* cited by examiner

*Primary Examiner* — Chris R Tate
*Assistant Examiner* — Russell Fiebig
(74) *Attorney, Agent, or Firm* — Stephen J. Scribner

(57) ABSTRACT

An electroporation apparatus provides for the electroporation of adherent cells attached to an electrode surface or suspended cells in close proximity to an electrode surface. In one embodiment, the electrodes are transparent to allow cell viewing using a microscope or an automated image analysis machine. The geometry of the electrodes and associated electrically non-conductive structures may provide for well-defined regions of electroporated and non-electroporated adherent cells with a clearly defined interface between these regions, facilitating comparison of electroporated cells and non-electroporated cells, and evaluation of transfer of material from cell to cell via intercellular gap junctions.

23 Claims, 14 Drawing Sheets

PLANAR ELECTROPORATION APPARATUS AND METHOD

RELATED APPLICATIONS

This application claims the benefit of the filing date of U.S. Provisional Patent Application No. 60/904,188, filed on Mar. 1, 2007, the contents of which are incorporated herein by reference in their entirety.

FIELD OF THE INVENTION

This invention relates to an apparatus and method for introducing material into cells through electroporation, by application of an electric field or current to the cells. The apparatus and method have broad applications in areas such as cell biology research and drug discovery.

BACKGROUND OF THE INVENTION

Early work by Zimmerman (U.S. Pat. No. 4,292,408), Sowers (U.S. Pat. No. 4,622,302) and Yaoita et al. (1988), among others, established that the outer cell membrane could be altered by the presence of a transient electric field. Much of the original interest in this process related to cellular fusion, where two or more cells are joined. The enduring technology, however, has been that of electroporation, where temporary pores are created in the outer cell membrane by the application of an electric field to allow material from the surrounding medium to move into the cell.

The treatment of suspended cells in a cuvette that has aluminum electrodes built into opposing walls has become a widely used electroporation technique. Commercial electroporation systems for this process are available from a number of lab instrumentation suppliers such as BioRad, BTX, Invitrogen and Eppendorf.

Initially, adherent cells were electroporated using suspension cell equipment by first detaching the cells from the substrate on which they were growing. Because this can substantially disturb adherent cells, various techniques were developed for subjecting adherent cells to an electric pulse without detaching them from the substrate. The BTX Petri Pulser™ is a commercially available unit consisting of a set of parallel, thin, gold coated plates that rest on edge in a Petri dish where cells are growing while a pulse is delivered between the plates which alternate in polarity. However, many cells are damaged in this process and cleaning the elaborate electrode set complicates the process.

Recently, techniques employing the processes used in microelectronic silicon chip manufacture have been applied to make "lab on a chip" systems that use electroporation to treat small numbers of suspended or adherent cells. Khine et al. (2005) describes a polymeric chip that can selectively immobilize and locally electroporate single cells. Yu-Cheng Lin et al. (2001) describes an electroporation microchip consisting of a defined cell culture cavity region with thin-film electrodes made of titanium and gold, fabricated on a glass slide using micro-fabrication technologies, which include evaporation, photolithography and wet-etching methods.

Continuing work in the field of electroporation indicates the need for a method for introducing materials into cells that is not well met by existing alternative procedures. Microinjection, where material is injected into cells through the cell wall using small stabilized needles, is very slow and requires expensive, sophisticated manipulators. Scrape loading, where a sharp blade slashes through a monolayer of adherent cells, can cause some cells to take in material through their wounded parts before healing. However, such harsh treatment of the cells raises concerns about the reliability of subsequent conclusions.

Calcium phosphate transfection predates electroporation and continues to be used though it is appropriate only for nucleic acids. Liposome transfection has also been used, though making appropriate liposomes containing the desired material and having them fuse with the cells complicates the process.

Over the past two decades, with advances in genetics research, the ability of electroporation to introduce genetic material into cells has been the application most in demand and it will continue to be very important. In recent years, research into the role of smaller molecules such as peptides, and the use of fluorescent markers for the study of cellular functions, are expanding the scope of applications involving electroporation, particularly with respect to adherent cells.

U.S. Pat. No. 5,232,856 to Firth describes a method for providing a uniform electric field over an area of cells growing on a conductive, transparent electrode made of indium tin oxide, by using a specific geometry of a second electrode in contact with the electroporation medium immediately above the cells. Boccaccio et al. (1998) demonstrates the efficacy of the technique for introducing small molecules into adherent cells.

The need for a method of quantifying the extent of gap junctions in adherent cells was highlighted in Fick et al. (1995) wherein it was noted that the microinjection technique in particular would require a prohibitively large number of experiments. Raptis et al. (2005) described how the apparatus disclosed in U.S. Pat. No. 5,232,856 may be employed to study populations of electroporated and non-electroporated cells as they grow side by side on a partially conductive microscope slide, how to observe whether cells have gap junctions, and how to determine the amount of gap junction communication that takes place. However, drawbacks to that technique include detachment of adherent cells during placement or removal of the upper electrode, and the inability to observe the cells until the upper electrode has been removed after the electroporation event.

SUMMARY OF THE INVENTION

A first aspect of the invention relates to an apparatus for electroporating cells, comprising: (a) first and second substantially coplanar electrodes positioned to create an electric field therebetween when connected to a source of electric potential; (b) containment means disposed on at least a portion of the first and second electrodes, that contains the cells in solution; and (c) an electrically non-conductive barrier disposed between the first and second electrodes that divides the containment means into first and second portions and directs at least a portion of the electric field thereover.

The first and second electrodes may each comprise a substrate and an electrically-conductive coating thereon, or they may together comprise a single substrate and an electrically-conductive coating thereon. The first and second electrodes may be substantially optically transparent.

The electrically non-conductive barrier may be of a height less than a height of the containment means. The barrier may divide the containment means into two or more portions and prevent transfer of cells between the two or more portions.

The electrically-conductive coating may comprise at least one of indium tin oxide (ITO), gold, doped indium oxide, cadmium oxide, cadmium stannate, zinc oxide, zinc cadmium sulfite or titanium nitride, antimony oxide, aluminum oxide, titanium oxide, copper indium oxide, and carbon nanotubes.

In one embodiment, at least one of the first and second portions of the containment means includes at least one electrically non-conductive region adjacent to and substantially coplanar with the first or second electrode.

The solution may be an electrolyte and may include material to be introduced into at least a portion of the cells. The material may be selected from proteins, peptides, nucleic acids (DNA, RNA, siRNA), compounds such as dyes, quantum dots, nanoparticles, carbon nanotubes, fluorescent markers, drugs, small molecules, viruses, and phages, and combinations and/or fragments thereof.

In one embodiment, the first and second electrodes comprise a microscope slide. In another embodiment, the apparatus may further comprise an electrically conductive barrier disposed on top of the electrically non-conductive barrier. In another embodiment, the apparatus may comprise a multi-well electroporation plate. The multi-well elecroporation plate may comprise a plurality of the electroporation apparatus described above, as an array. In a further embodiment, the first and/or the second coplanar electrode may comprise one or more electrically isolated region.

The electroporation apparatus or the multi-well electroporation plate may be combined with one or more of a microscope, digital camera, image analysis software, computer, and robotic equipment for introducing cells and materials into the well(s). These may be combined in a system for automated electroporation and analysis of cells, including at least one automated function selected from fluid handling, electroporation pulse delivery, image capture, and image analysis, optionally including analysis of cellular responses to materials introduced by electroporation. This process is particularly amenable to the use of quantum dots as fluorescent markers when such markers are structured to emit light of a specific wavelength after being incorporated into some cellular component. That is, there is no potentially confounding background fluorescence, which is not the case when using constitutively fluorescent materials such as Lucifer Yellow.

Another aspect of the invention relates to a method for electroporating cells, comprising: (a) maintaining the cells in a solution on or above first and/or second substantially coplanar electrodes separated by an electrically non-conductive barrier and positioned to create an electric field therebetween when connected to a source of electric potential, the solution covering the electrically non-conductive barrier and comprising an electrolyte and material to be introduced into the cells; and (b) applying an electric potential to the first and second electrodes, wherein an electric field resulting from the electric potential is established over the electrically non-conductive barrier between the first and second electrodes; and wherein the electric field causes electroporation of at least a portion of the cells.

In one embodiment, the method may further comprise disposing an electrically conductive barrier on the electrically non-conductive barrier, the solution covering the electrically non-conductive barrier and contacting the electrically conductive barrier; wherein the electric field is established over the electrically non-conductive barrier and through the electrically conductive barrier.

The method may comprise maintaining adherent cells and/or suspended cells on or above the first and/or second electrodes. The method may additionally comprise maintaining the cells on or above a non-conducting region of a substrate that is adjacent to and substantially coplanar with at least one of the first and second electrodes; wherein the electric field causes electroporation of cells on or above a said first or second electrode and does not cause electroporation of cells on or above a said non-conducting region, such that regions of electroporated and non-electroporated cells are established about a line corresponding to a juncture of a non-conducting region and an electrode.

The method may further comprise: providing one or more electrically isolated region within the first and/or the second coplanar electrode; wherein cells associated with the one or more electrically isolated region are substantially not electroporated.

Another aspect of the invention relates to a method for assessing gap junctions in cells, comprising: subjecting cells to the method described above, wherein one or more electrically isolated region is provided within the first and/or the second coplanar electrode and cells associated with the one or more electrically isolated region are substantially not electroporated; and monitoring transfer of material from electroporated cells to cells not electroporated; wherein transfer of material is indicative of gap junctions between cells.

The invention may provide for electroporating hundreds or thousands of cells at the same time as they grow on, or are in suspension above transparent, substantially co-planar electrodes. One particularly useful embodiment of the invention relates to a process whereby regions of electroporated cells and regions of non-electroporated cells are adjacent to one another and are clearly defined. While useful for a variety of electroporation related applications, the invention is particularly well suited to the evaluation of intercellular gap junction communication.

In another aspect, the invention seeks to provide an improved method for electroporating cells on a conductive surface, such as a microscope slide, without the use of an upper electrode placed opposite the surface on which the cells to be electroporated are growing or are suspended. Instead, according to the invention, two electrodes are disposed in a substantially coplanar relationship, with a non-conductive barrier disposed therebetween, such that the electrical path from the first electrode to the second electrode is over the barrier through the liquid buffer in which the cells are immersed. The displacement of the electric field over the barrier results in electroporation of cells on the electrodes and/or suspended in the buffer at least in proximity to the barrier. Moreover, by varying one or more of the geometrical arrangement of the electrodes, the arrangement of the barrier, and the characteristics of the electric potential/field applied to the cells, control over the region of cells electroporated within the total cell population may be gained.

In accordance with one embodiment of the invention, living cells are grow on or above a substrate, part of which is electrically conductive and part of which is not electrically conductive. The cells associated with the electrically conductive part of the substrate are subjected to an electric stimulation causing temporary pores to form in the cell membrane. During the time that the stimulated cells have open pores, material from the surrounding medium may enter these cells. Subsequently, the pores close, resulting in two adjacent populations of cells; one population associated with the electrically conductive part of the substrate that has taken in material from the surrounding medium and a second, distinct population of cells that has not taken in said material.

BRIEF DESCRIPTION OF THE FIGURES

For a more complete understanding of the invention and to show more clearly how it may be carried out, the invention will be described by way of example with reference to the accompanying figures, wherein.

DESCRIPTION OF PREFERRED EMBODIMENTS

Figure 1:
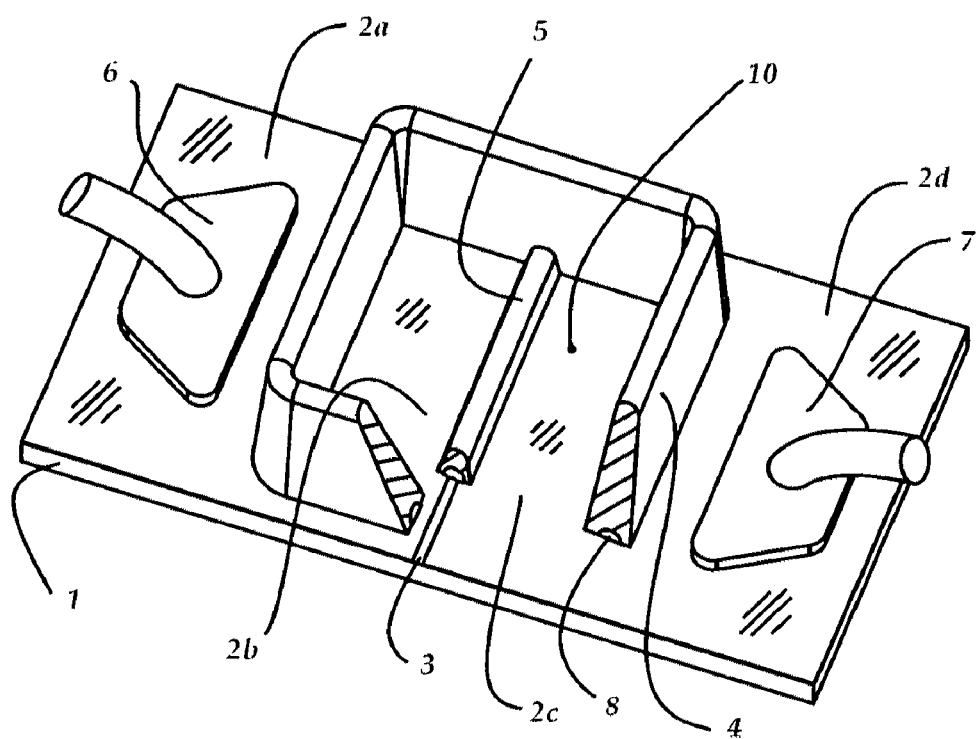
FIG. 1 shows an embodiment of an electroporation apparatus of the invention comprising a substrate that has regions that are coated with conductive indium tin oxide (ITO), a narrow line of bare substrate, a well for containing cell growth medium and electroporation medium (shown with a cutaway for clarity), and a low dividing wall across the well covering the bare substrate line, and electrical contacts that are used to apply a voltage to the conductive ITO regions.

Previous electroporation devices suffer from drawbacks including the inability to observe cells before, during, and/or after electroporation without disturbing the cells, the inability to electroporate large numbers of cells, and the inability to control electroporation within a population of cells in the electroporation device.

The invention seeks to overcome such drawbacks of previous devices by providing an electroporation apparatus having planar electrodes and a dielectric barrier disposed between the planar electrodes for controlling the electric field and thereby controlling electroporation of cells. Insofar as planar arrangement of electrodes has been incorporated in previous devices, such devices are either high throughput arrays that do not allow for observation of cells (e.g., U.S. Pat. No. 6,352,853 to King et al.), or have interdigitated electrode arrangements for electrotransformation of individual cells (e.g., U.S. Pat. No. 5,137,817 to Busta et al.) or for electrofusion of multiple cells (e.g., U.S. Pat. No. 4,832,814 to Root), which do not permit control of electroporation within the cell population. U.S. Pat. No. 6,482,619 to Rubinsky et al. disclosed a microdiffusion apparatus for introducing materials into a single cell. That apparatus did not use an electric field and instead relied on mass transfer across the cell membrane achieved by exposing the cell to liquids of different compositions through a complex arrangement of channels.

One aspect of the invention relates to an apparatus for electroporating cells, comprising a substrate, at least a portion of which is electrically conductive, a well disposed on the substrate that contains the cells and suitable media and/or buffers, and in which are disposed planar electrodes for electroporating the cells, a dielectric barrier disposed between the planar electrodes, and electrical contacts at opposite sides of the well. The cells may be grown on the substrate (i.e., adherent cells), or the cells may be grown in suspension above the substrate. The substrate may also be substantially optically transparent, so as to facilitate observation of the cells with a light microscope or other optical apparatus. Materials to be introduced into cells via electroporation may include, but are not limited to biological molecules such as proteins, peptides, nucleic acids (DNA, RNA, siRNA), compounds such as dyes, quantum dots, nanoparticles, carbon nanotubes, fluorescent markers, drugs, small molecules, viruses, and phages, and combinations and/or fragments thereof.

Planar electrodes avoid the need for an electrode positioned above the cells. The lack of an electrode above the cells allows the cells to be observed before, during, and/or after electroporation, using, for example, a light microscope, without disturbing the cells or manipulating the apparatus. Further, the lack of an opposing electrode avoids the possibility of disturbing cells as may occur upon removal of the upper electrode.

An electroporation apparatus as described herein is cost effective to use because it allows for the amount of reagent(s) (e.g., material to be introduced into the cells) required to be minimized, as such reagents may be expensive and difficult to obtain. The electroporation apparatus allows for the study of only a small quantity of treated (i.e., electroporated) cells, or it may easily be scaled up to treat millions of cells. The apparatus is therefore suitable for one-off experiments involving only a small sample of cells, as well as for scaling up to a fully automated system that can process hundreds of samples per hour. The apparatus also allows for comparing electroporated and non-electroporated (i.e., control) cells on the same substrate (e.g., growing side by side), both groups having shared all of the same experimental steps except for electroporation.

One embodiment of the electroporation apparatus will now be described with reference to FIG. 1. A well 10 in which cells are contained is formed by a wall 4, shown in cutaway view, on a substrate 1. The height of the wall 4 is not critical so long as it is high enough to contain the cells and the liquid growth and/or electroporation media. The height may be set as required for a particular application or experiment. The wall 4 may be bonded to the substrate by an adhesive, which is preferably hydrophobic, such as a silicone adhesive, optionally with a gasket of a plastic material that also acts as a hydrophobic border for the cell growth region. The wall 4 may include regions that are shaped to minimize fluid turbulence experienced by the cells when fluid is added to or removed from the well. Such features may be advantageous in both manual and automated applications.

The substrate 1 is coated with an electrically conductive coating that is suitable (i.e., non-toxic) for cell growth, such as, but not limited to, indium tin oxide (ITO), gold, doped indium oxide, cadmium oxide, cadmium stannate, zinc oxide, zinc cadmium sulfite or titanium nitride, antimony oxide, aluminum oxide, titanium oxide, copper indium oxide, or carbon nanotube based material, or a combination thereof. Insofar as it may be desirable to observe cells in the well using light transmitted through the substrate 1, the substrate and the electrically conductive coating may be substantially optically transparent. The substrate may therefore be made of glass, polycarbonate material, plastic, or other suitable material. Advantageously, the electroporation apparatus may be constructed on a standard microscope slide, or made so as to be compatible with a standard microscope slide in terms of the ability to observe cells in the apparatus on a microscope. The coating may be ITO which is substantially transparent. However, other substrate materials and coatings may also be used. A portion 3 of the substrate 1 is not covered by the electrically conductive coating, so as to form two electrodes 2b, 2c within the well. The electrodes 2b, 2c are coplanar in that they lie in a substantially common plane which in this embodiment is defined by the substrate 1. The two electrodes may be formed by removing a strip of the coating from the substrate in the region where the well is to be located and the cells are to grow. For example, the portion of substrate not covered by the coating may be located across the central region of the substrate 1.

It should be noted that the two electrodes need not be made of the same substrate material and/or of the same electrical coating. Also, it is not necessary that both electrodes be either optically transparent or not optically transparent. Rather, different combinations of materials may be used for each of the two electrodes. The embodiment described below with respect to FIG. 7 more conveniently provides for such different materials for the two electrodes.

As shown in FIG. 1, a lower wall 5, also referred to herein as a barrier, divides the well into two portions which may or may not be equal in area. The height of the barrier may be high enough to create a separation of the cells on either side. It may also be desirable to provide different growth media or buffers to the cells on either side of the barrier and therefore the barrier should be high enough to prevent transfer of the cell growth medium or buffer from one side to the other. The barrier 5 may be of the same material as the wall 4, and attached to the substrate over the portion 3 not covered by the electrically conductive coating in the same manner as the wall 4 is attached to the substrate. The barrier 5 is also attached to the wall 4 at each end, so as to form a complete barrier across the well 10, such that when the level of the medium or buffer above the cells is lower than the barrier height (e.g., less than 1 mm deep), then there is no liquid connection between the two sides 2b, 2c of the barrier 5.

Cells may be grown on either side of the barrier 5 or on both sides of the barrier 5 inside the well. During the cell growth period the medium inside the enclosed area may be so deep as to cover the barrier 5. However, it may be desirable to have a different medium or buffer on either side of the barrier, in which case the levels of the media or buffers should of course be kept below the barrier. A lid, not shown, may be used to cover the top of the well, and it may be desirable to provide a gap for gas exchange while the cells are growing.

Figure 12:
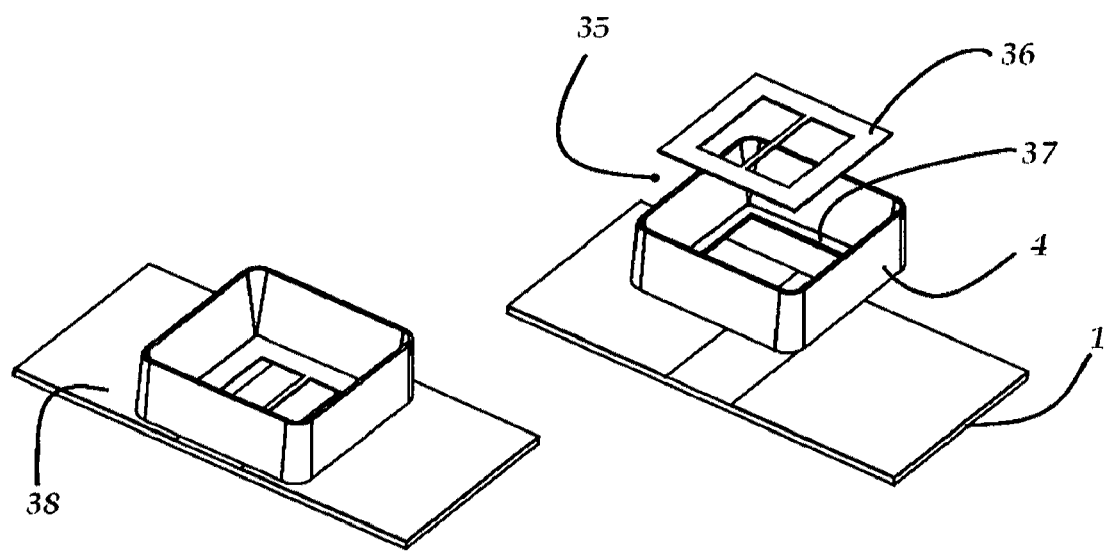
FIG. 12 shows an electroporation apparatus in which the wall which forms the electroporation well is bonded to the substrate using an adhesive gasket which also defines the cell growth area and provides for attachment of the central barrier.

The wall 4 that forms the well 10, and the barrier 5, may be made of a plastic material, and these may be bonded to coated and non-coated regions of substrate I using a suitable adhesive such as medical grade silicone. Preferably the adhesive is formulated to allow the wall 4 and barrier 5 to be easily peeled away from the substrate surface, permitting the cells to be covered with a cover slip and viewed with a light microscope. For example, as shown in FIG. 12, the wall 4 and barrier 5 may be bonded to the substrate 1 using an adhesive-backed gasket 36, made of a suitable material such as Nylon™ or Teflon™. The wall 4 may have a flange 37 at its base to provide a bonding area for the gasket 36. The gasket bonds itself and wall 4 to the substrate 1 resulting in the assembly 38.

Two electrical contacts 6,7 are disposed one on either side of the well. These provide electrical connections to the conductive surfaces 2a, 2d of the substrate 1 and are preferably made of a flexible conductive metal. For example, a coiled spring may be used to provide multiple contact points.

For electroporating the cells, the growth medium in the well is replaced with an electroporation buffer (i.e., an electrolytic liquid) containing the material to be introduced into the cells. The well is filled to a depth sufficient to cover the barrier 5, to ensure that the buffer connects the two sides of the well. The electrical contacts 6, 7, which are located at opposite sides of the well 10, are connected to an AC or DC source of electricity, such as a pulse generator. An electric current, typically in the form of a series of electric pulses, is delivered through the circuit of the source, the first electrical contact 6, the coated substrate 2a, through the conductive coating, beneath the nearest wall 4 of the well 10, to the region below the cells 2b and the buffer on the near side of the well, up through the cells and the buffer above them, through the buffer over the barrier 5, down through the buffer and the cells on the other side of the barrier, into the conductive coating 2c, through this coating under the wall of the well to the coating surface 2d beneath the second electrical contact 7, and then back to the source of electricity.

Insofar as it may be either an electric field or an electric current which causes a transient opening in the cell membrane required for electroporation, the terms "field" and "current" are used interchangeably throughout this disclosure and use of one of these terms shall not be construed as exclusive of the other or as limiting in any way.

A variety of electric pulse shapes and patterns have been described in patent and scientific literature relating to electroporation, and many such pulse shapes and patterns are suitable for use with the invention. For example, for electroporation on an ITO slide, square waves, capacitor discharge pulses, and oscillating waves will all produce results. For this invention, it has been found to be beneficial to administer at least 4 pulses and to have them delivered with alternating polarity. However, it is considered routine that the normally skilled artisan will experiment with different pulse shapes and patterns to determine a suitable protocol for a given set of conditions and cell type.

In comparison to suspension cell electroporation, adherent cell electroporation requires relatively low voltages and small amounts of total energy in order to cause pores to form in the outer cell membrane. This sensitivity of cells to electrical stimulation when they are attached to an electrode, often in a flattened, elongated state as opposed to the spherical shape of a cell in suspension, can be problematic in that even small amounts of electrical energy can cause damage or destruction of the cell membrane.

A further challenge in electroporating a large number of adherent cells at once is to provide an amount of electrical stimulation to the cells growing on an area of an electrode surface, wherein the electrical stimulation falls within the range of what is sufficient to cause electroporation without destroying the cells.

The inventors have found that a variety of pulse shapes and pulse combinations may be used to electroporate cells. Which of these is best is often influenced by the geometry of the electrodes, the types of cells being targeted, and the electroporation buffer characteristics. Experimentation with a coplanar electrode configuration as described herein has shown the following characteristics, described below, to be significant in achieving uniform electroporation of cell groups in the order of square millimeters in area, with minimal or no cell death.

Figure 2:
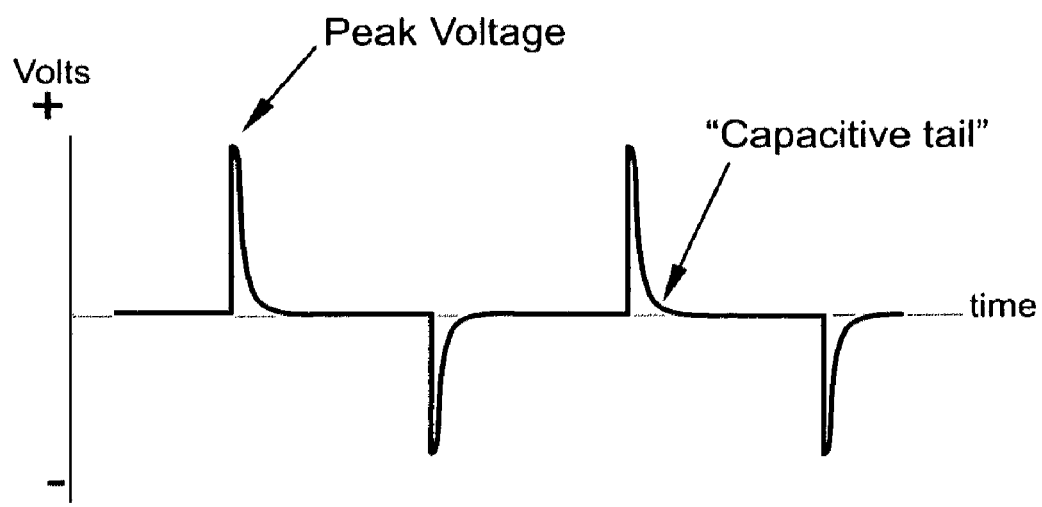
FIG. 2 shows an example of an electrical pulse train suitable for use with an electroporation apparatus as described herein.

Using a DMEM (Dulbecco's modified Eagle's medium) electroporation buffer, with cells growing on conductive ITO electrodes which have a surface resistivity of 20 ohms/square, it was found that the voltage, pulse width, number of pulses, polarity of pulses, and pulse shape contributed to the efficacy of successfully and uniformly electroporating a group of cells spread over an area. While it was possible to cause electroporation using a single pulse, it was found that multiple pulses having a lower initial voltage and shorter pulse durations than a single longer pulse were more effective, resulting in uniform electroporation over a larger area of cells. For example, in the case mentioned above, pulse trains of about 4 to 20 pulses with voltage of between about 5 and about 50 volts were effective. Whereas a single pulse width of 10 milliseconds or more destroyed most of the cells, even at low voltage settings, it was found that sequences of pulses of lengths between about 1 microsecond and about 1000 microseconds were useful. In general, it was found that pulse widths of between about 10 and about 500 microseconds yielded good results. Pulse spacing of from about 10 microseconds to about 10 seconds, or about 100 microseconds to about 1 second, is suitable. For planar electroporation as described herein, short pulses having a capacitive discharge-like tail (see FIG. 2) have proven most effective. Further, to avoid a buildup of ions in the region close to the electrode surface, the sequence of pulses may be provided alternating polarity.

To give an example of a configuration of the embodiment of FIG. 1 suitable for general use, the substrate may be a standard microscope slide coated with ITO (resistivity of 15 ohms/square) to a thickness of 120 nm. The two electrodes may be formed by removing a strip of the coating about 0.3 mm wide from the central region of the substrate where the well is to be located and the cells grown. The wall height of the well may be about 8 mm, and the height of the barrier may be about 2 mm. For many cell types, an electroporation buffer that is predominantly DMEM, and an electroporation pulse such as a capacitive pulse delivered from a 0.5 microfarad capacitor that has been charged to 25 volts and discharged across the substrate 6 times at 2 second intervals with alternating polarity, are suitable, and will result in more than 50% of the cells in the well being electroporated. However, this example should not be construed as limiting in any way.

Those skilled in the art will understand that the resistance of the various components making up the electrical circuit will have an influence on the optimal parameters for the electroporation pulses. ITO coated glass and plastic is available commercially with surface resistivity values ranging from 2 to 200 ohms per square. The quality of the electrical connection between the contacts and the coating is an important consideration. It may vary depending the on the materials used, the shapes of the components, and the pressure with which they are applied to the surface. The latter may be the most important to control in order to maintain consistency from experiment to experiment.

The electrical characteristics of the electroporation buffer may also play a significant role in determining the overall circuit impedance. While it is essential that the buffer is in electrical contact with the two sections 2b, 2c of coated substrate, it should be noted that the behaviour of the buffer is not the same as that of a conducting wire. While there is some flow of charge carriers through the buffer, a significant contribution to the passing of current from one electrical contact to the other is a result of ionization of molecules at the coating-electroporation buffer interface. This is why it is helpful to alternate the polarity of the pulses being delivered.

A useful feature of the invention is the ability to selectivity create regions of electroporated cells and non-electroporated cells within a population of cells in the well, which may be of interest in certain studies. Without wishing to be bound by theory, it is believed that this selectivity results from the substantially vertical electric field induced by the presence of the barrier, which forces the electric current to flow substantially perpendicular to the substrate. The geometrical arrangement of the well, the barrier, and the electrodes may therefore be set to provide for a desired region of cells to be electroporated. For example, increasing the length of the well 10 along the axis perpendicular to the barrier 5 will reduce the likelihood that cells furthest from the barrier will be electroporated. However, increasing the height of the barrier will extend the region of electroporated cells farther from the barrier. Again without wishing to be bound by theory, it is believed that this is because the electric current passes through the coating beneath the cells and does not create a significant electric field across the cells until it reaches a point close to the barrier, where the electric field moves up through the buffer and over the barrier. That is, the arrangement of the barrier and electrodes may establish a non-uniform or graded electric field with the field strength being strongest closest to the barrier, which may advantageously be used to create regions of electroporated cells and regions of non-electroporated cells in the same well.

For example, to electroporate most of the cells in the well, the electrode areas 2b and 2c should be elongated along the axis parallel to the barrier and short along the axis that is perpendicular to the barrier. Alternatively, a geometry where the electrode areas 2b and 2c are short along the axis parallel to the barrier and elongated along the axis that is perpendicular to the barrier will result in a region of electroporated cells close to the barrier and a region of non-electroporated cells furthest from the barrier.

As an example, an electroporation apparatus was constructed on a substrate with an ITO coating having resistivity of 15 ohm/square, a barrier 0.8 mm high and a Teflon™ well wall height of 2 mm which defined a well area 8 mm along the barrier and 6 mm away from the barrier. Using a 0.1 microfarad capacitor discharged 6 times with an initial voltage of 25 volts and alternating the polarity of each subsequent pulse, it was found that electroporation of cells was most consistent within about 5 mm of the barrier. These parameters may be used to optimize the design of the electroporation apparatus for a given application.

If the barrier was omitted, only a line of cells (e.g., one or two cells wide) on each edge of the etched line 3 would be electroporated. On the non-conductive substrate region of the etched line 3 between the coated areas 2b and 2c, cells would be either unaffected or completely electroporated depending on whether or not they were electrically coupled by gap junctions. Such a configuration is the subject of a separate application. For the invention disclosed herein, it is desired to achieve wider areas of electroporated cells which can be obtained by including the central barrier and forcing the electric field to flow through the electroporation buffer and spread across a broader area of cells.

Those skilled in the art and with access to various grades of coated substrates will find that using different combinations of coating conductivity with electroporation buffers of various conductivity can extend the strength of the electric field away from the barrier, and thus extend the area of electroporated cells away from the barrier to varying degrees with, for example, 1 mm being easily achieved and more than, for example, 3 mm requiring optimization. Using buffers that are less conductive, such as those based on a saline solution, can improve the system performance where a coating with a relatively high surface resistivity is used.

It is also noted that some cell types are more easily electroporated than others. Some cell lines are difficult to handle because they do not adhere firmly to the coating or they come off the substrate after the electroporation pulse. Furthermore, cell density, i.e., how much of the surface of the well they cover, can have an effect on the pulse parameters required to achieve optimal electroporation. For this reason, a pulse generator that allows for adjustment of the pulse parameters is recommended.

In some cases it may be useful or necessary to have the cells grow on an intermediary layer of material which coats the electrode surface. For example, for cells that do not bond strongly to the coated electrode surface, materials such as collagen or commercial products such as BD Cell-Tak may be used. These are compatible with coplanar electroporation as described herein, although their use may require an increase in the intensity and/or duration of electrical stimulation to compensate for the added resistance of the coating.

Another coating application is the bonding of materials of interest to the electrode surface so that such materials will be in proximity to the cells during the electroporation event. For example, a thin-film that releases entrapped materials of interest, such as pharmaceutical compounds, by disintegrating when subjected to an electric field, may be used. In such a thin-film system, the material may be sandwiched and held in place until an electrical potential is applied to the film, which causes the film to disintegrate and release the material (see, e.g., Wood et al., 2008). Such an arrangement would work well with an electroporation process such as that described herein, whereby the electrical pulse would simultaneously release the material and open pores in the cells.

Figure 3:
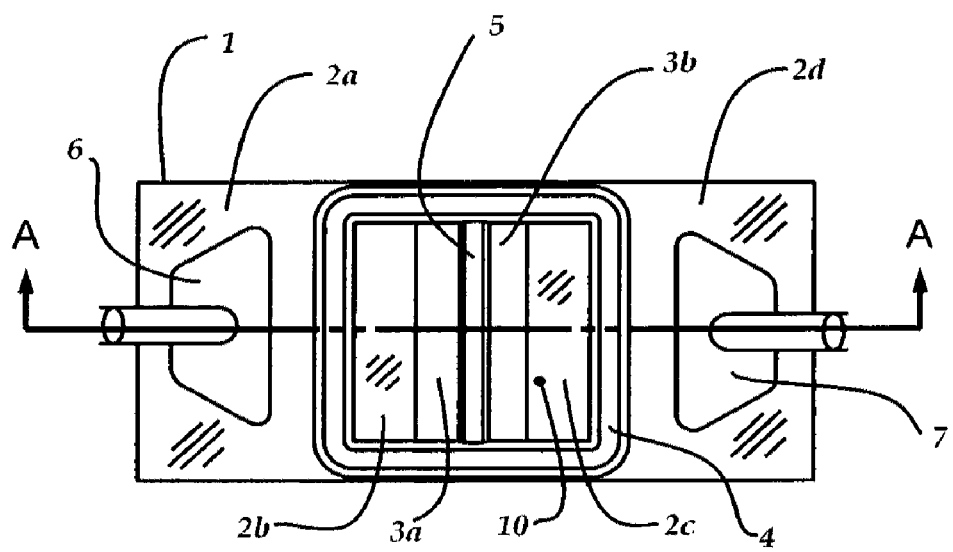
FIG. 3 shows another embodiment of an electroporation apparatus of the invention comprising a substrate that has regions that are coated with conductive ITO, regions that are bare substrate, a well for containing cell growth medium and electroporation medium, a low dividing wall across the well, and electrical contacts that are used to apply a voltage to the conductive ITO regions.
Figure 4:
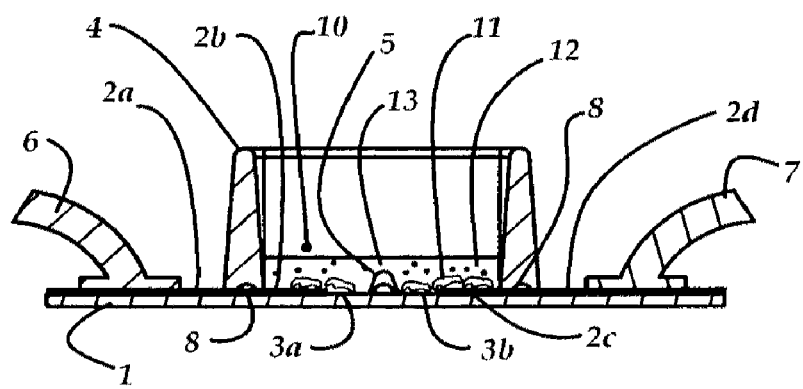
FIG. 4 shows the embodiment of FIG. 3 in a sectional view along a line A-A and shows electroporation fluid and growing cells which are enlarged for clarity.
Figure 5:
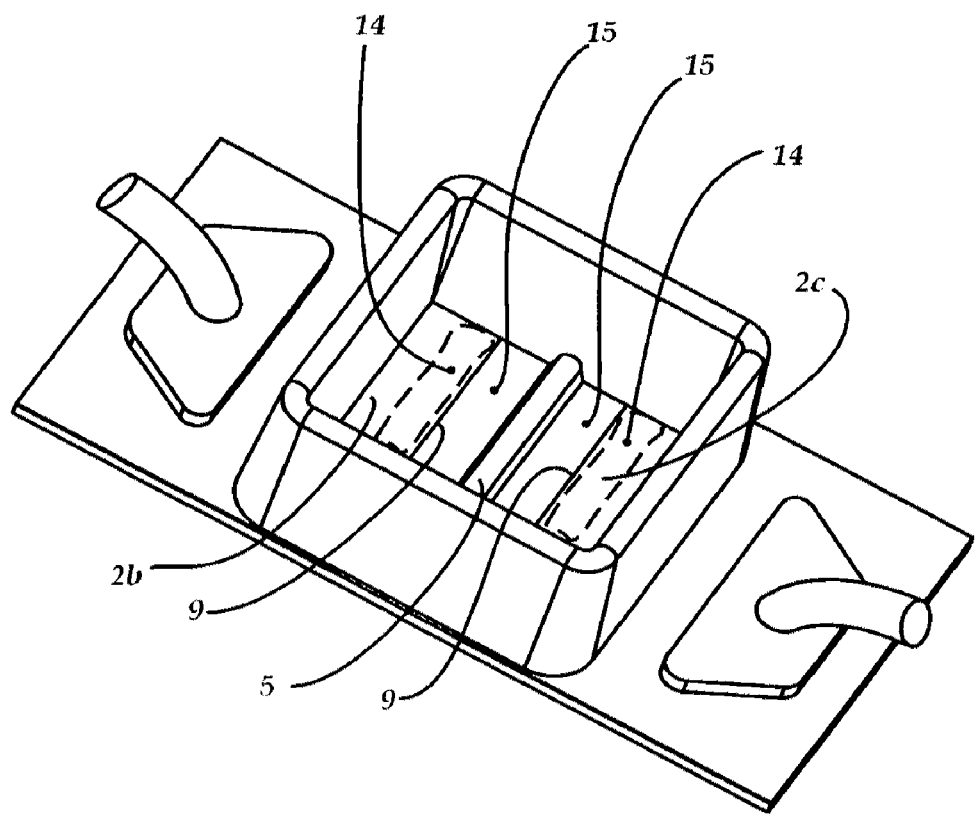
FIG. 5 shows the embodiment of FIG. 3 having areas on the substrate where electroporated cells are immediately adjacent non-electroporated cells.

In another embodiment, shown in FIGS. 3, 4, and 5, the substrate 1 is coated in part with an electrically conductive coating, such as, for example, ITO, in regions 2a, 2b, 2c, 2d. The substrate and coating are preferably substantially transparent such that a microscope may be used to view cells growing thereon. In this embodiment the barrier 5 separates the uncoated substrate areas 3a, 3b, and the coplanar electrodes 2b, 2c. The uncoated areas may be, for example, 5 mm wide. As in the previous embodiment, a wall 4 is bonded to the substrate, defining the well 10 where the cells grow.

FIG. 4 shows a sectional view of the embodiment of FIG. 3 along the centerline A-A. In this view the cells 11 and electroporation buffer 12 are shown. Note that the electroporation buffer fills the well 10 to a depth that provides for a fluid connection 13 from the conductive surface 2b over the dividing barrier 5 to the conductive surface 2c. The cells 11, which are shown enlarged for clarity, grow over the transition from the conductive regions 2b, 2c to the non-conductive regions 3a, 3b of the substrate.

FIG. 5 shows regions 14 on the conductive area of the substrate where electroporation takes place and regions 15 where no electroporation takes place because there is no conductive coating on the substrate. These regions are defined by the transition 9 between the conductive regions 2b, 2c and the non-conductive regions 3a, 3b of the substrate. This produces a corresponding transition line between electroporated cells and non-electroporated cells. Providing a sharp, well-defined transition line 9 (e.g., one that is an order of magnitude less than the size of the cells) ensures that electroporated cells and non-electroporated cells may be clearly identified. Of course, the size of the region 14 of electroporated cells may vary as a function of one or more factors including, for example, cell type, conductivity of the electroporation buffer, resistivity of the conductive coating, and size of the conductive surface 2b and/or 2c on which the cells are growing. Accordingly, one or more of these factors may be adjusted so as to achieve a desired size of the region 14 of electroporated cells.

Figure 8:
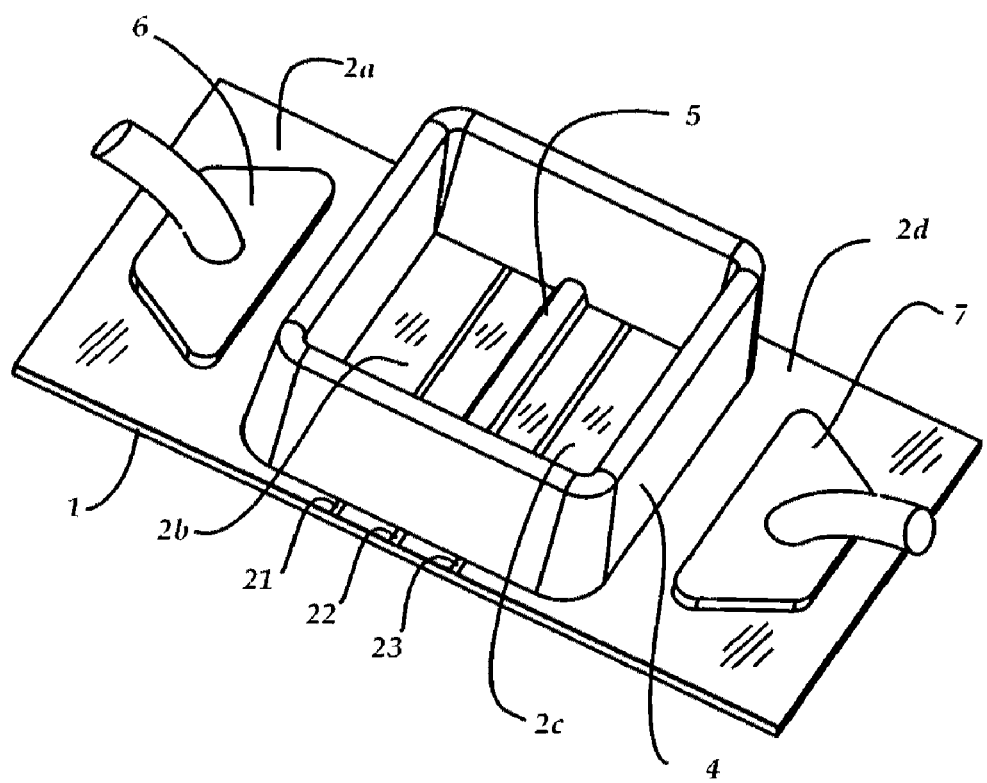
FIG. 8 shows an embodiment of an electroporation apparatus of the invention wherein lines of ITO have been removed, separating areas of conductive ITO, and additional visual reference marks have been made in the substrate.

In an alternative embodiment, the regions 14 of electroporated cells and 15 of non-electroporated cells may be provided by also having the conductive coating on the region 15, but having the coated regions 14 and 15 electrically isolated from each other by a non-conductive line therebetween. For example, the conductive coating may be etched away so as to provide a non-conductive line between the regions 14 and 15. Such an embodiment is shown in FIG. 8, where electrical isolation of coplanar electrodes 2b and 2c is achieved with etched lines 21, 22, and 23. Using laser etching these lines can be made very precisely and without the chemicals required for photo etching.

Figure 9:
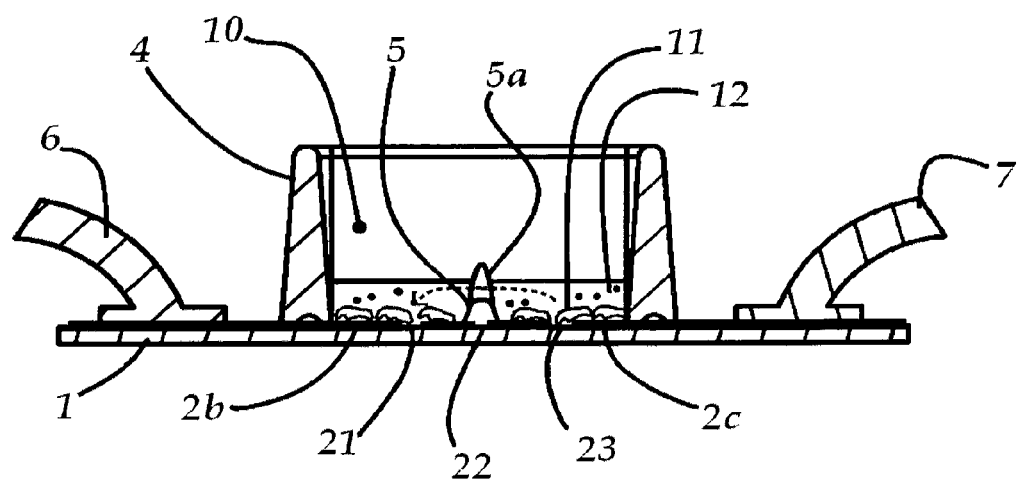
FIG. 9 shows an embodiment of an electroporation apparatus which is similar to the embodiment of FIG. 8, but includes a conductive portion added to the barrier.

A further embodiment of the electroporation apparatus is shown in FIG. 9. This embodiment, like that of FIG. 8, has lines 21, 22, 23 where the conductive coating has been removed from the substrate 1, forming electrically isolated regions of coated substrate immediately adjacent either side of the insulating barrier 5. However, this embodiment has a conductive portion 5a added to the top of the barrier 5. With this arrangement the electroporation solution does not have to be so deep as to cover the conductive portion 5a of the barrier, because the electrical path flows through the conductive portion as shown by the dashed line in FIG. 9. The principle of operation of this embodiment is therefore the same as other embodiments described herein, while, with this embodiment, it is possible to have a different electroporation solution on either side of the barrier. It will be appreciated that the conductive portion 5a may be added to the barrier of any of the embodiments described herein, including multi-well embodiments, to further increase the flexibility of planar electroporation in accordance with the invention.

Figures 6A, 6B, 6C, 6D:
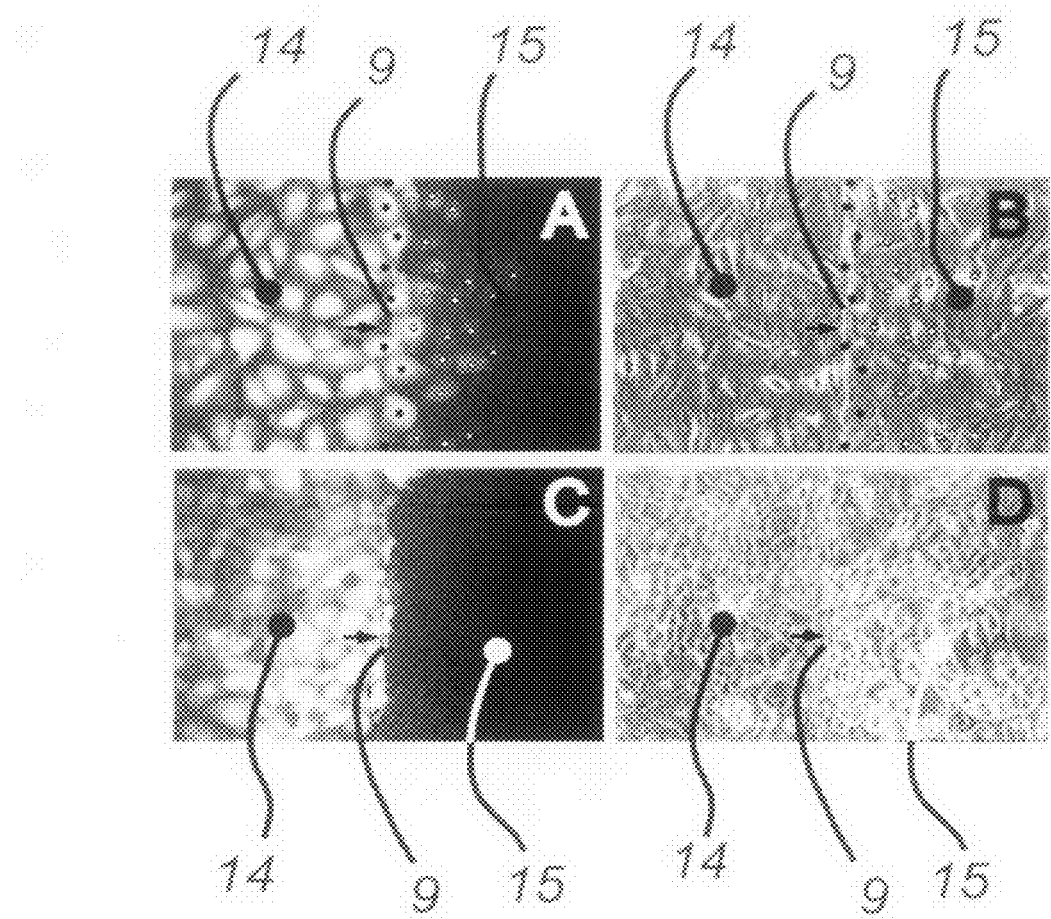
FIGS. 6A to 6D are photomicrographs showing normal mouse lung cells (A fluorescence micrcoscopy and B bright field view of these cells) and mouse lung tumour cells (C fluorescence microscopy and D bright field view of these cells), Lucifer Yellow UV sensitive dye having been electroporated into the cells on the left side of each figure allows for determining, by comparing A and C, that normal mouse lung cells have gap junctions by which fluorescent material has been passed to cells to the right of the electroporated region in A, while in C the tumour cells do not pass the fluorescent marker.

FIG. 6 shows photomicrographs (magnification 140×) of normal mouse lung cells (6A and 6B) and mouse lung tumour cells (6C and 6D) that have been electroporated in the presence of the fluorescent marker Lucifer Yellow. Images 6A and 6B are of the same field and show cells that have gap junctions. 6A is taken under UV fluorescence while 6B is taken under phase-contrast illumination. The arrow points to the transition line 9 between electroporated cells (left) and non-electroporated cells (right). This line corresponds to the transition between the conductive region 14 and the non-conductive region 15 of the embodiment of FIG. 5. FIGS. 6A and 6B also show the transfer of fluorescent material that occurs from the electroporated cells across the transition line 9 to the non-electroporated cells.

On close inspection the transition line 9 is visible through the cells in FIG. 6A and it is clearly seen with bright field illumination in FIG. 6B. Those skilled in the art will appreciate that a combination of image capturing hardware and appropriate software may be used to record the progression of fluorescence into the non-electroporated region and provide a quantification of the gap junctional intercellular communication taking place. The asterisks and dots in FIGS. 6A and 6B illustrate a manual method of counting source cells and cells taking up the fluorescent marker such that a ratio or other indicia of cellular communication may be established.

FIGS. 6C and 6D show adherent cells that do not have gap junctions. In FIG. 6D a bright field view clearly shows the presence of cells on the non-conductive region 15 of the slide; however, the electroporated cells in region 14 do not transfer any fluorescence across the transition line 9.

Figures 6E, 6F, 6G, 6H:
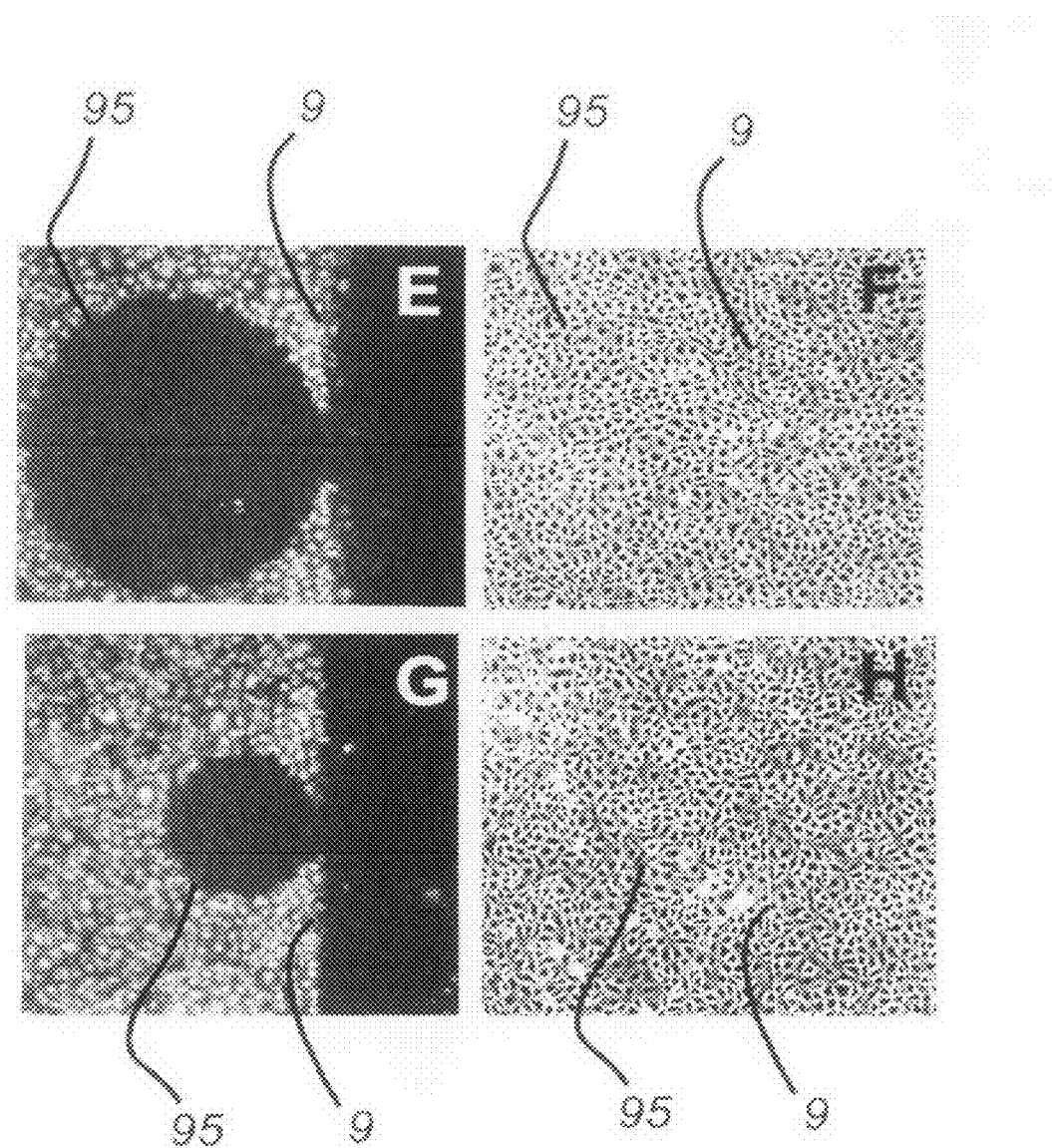
FIGS. 6E to 6H are photomicrographs showing A549 cells growing on electrically conductive and electrically isolated regions of an electrode, so as to define regions of electroprated and non-electroporated cells.

A further embodiment may include coplanar electrodes that have, in place of or in addition to an etched line such as 21, 23, regions bounded by an etched line such that they are electrically isolated. FIG. 6E is a photomicrograph of A549 cells on a substrate where a laser has been used to remove a 20 micron wide line of the ITO coating, so as to define the shape of a circle. The cells were electroporated with the fluorescent marker Lucifer Yellow, and cells that have taken up the fluorescent marker are glowing under UV light stimulation.

FIG. 6E shows a large circle 95 under fluorescence microscopy and FIG. 6F shows the circle and cells with phase contrast lighting. As can be observed, the A549 cell line does not have gap junctions and there is no transfer of the fluorescent marker from the glowing cells at the perimeter of the circle in FIG. 6E to the cells growing within the circle. FIGS. 6G and 6H show the same pattern with a smaller circle.

While this pattern of electrically isolated regions within the area of cells that are being electroporated provides a similar opportunity for gap junction analysis to that shown in FIGS. 6A to 6D, there are benefits to having a defined pattern. For example, by using laser or other etching methods, precisely-sized features of any shape may be provided in the substrate. This may allow an investigator to more easily visually judge the extent of gap junctions by knowing the size and/or dimensions of the shape used. For example, a rectangle which is separated from the transition line by, e.g., 10 rows of cells, and extends away from the barrier 5 of the well, may provide a further opportunity to study gap junctions. By extension, an automated vision system could take advantage of such a feature. Further, this method of analyzing gap junctions may be extended to the creation of a standard reference system. For example, by providing circles or other shapes of progressively larger sizes, e.g., 200, 400, 600, and 800 micron diameter circles, the transfer of a marker could be evaluated quickly according to the largest circle that was completely covered by marked cells.

Thus, using this technique, any shape, size, or pattern of conducting and non-conducting substrate may be produced, customized, etc., for particular applications such as studying gap junctions.

Figure 7:
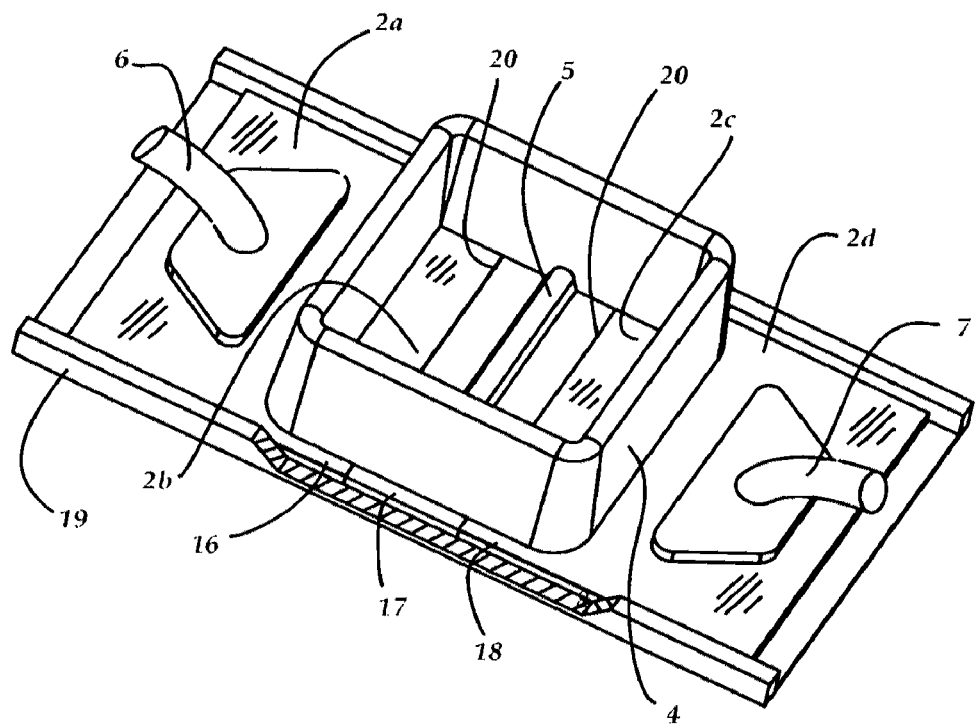
FIG. 7 shows another embodiment of an electroporation apparatus of the invention wherein the substrate comprises separate pieces which are used to form the base of the chamber on which the cells grow.

FIG. 7 illustrates another embodiment of the invention where the coplanar electrodes 2a, 2b and 2c, 2d are made from separate substrates 16 and 18 each having a conductive coating. A third substrate 17, which does not have a conductive coating, separates substrates 16 and 18 and is substantially coplanar therewith. All three substrates 16, 17, 18 are fixed to a carrier 19 which is shown with a cutaway to reveal the joining edges of the supported components. To facilitate cell growth over the joints 20 between substrates 16, 17, 18, the edges should fit together closely so as to avoid gaps, and the substrates should be of substantially the same thickness. With this embodiment no etching of the conductive coating is required.

Figure 10:
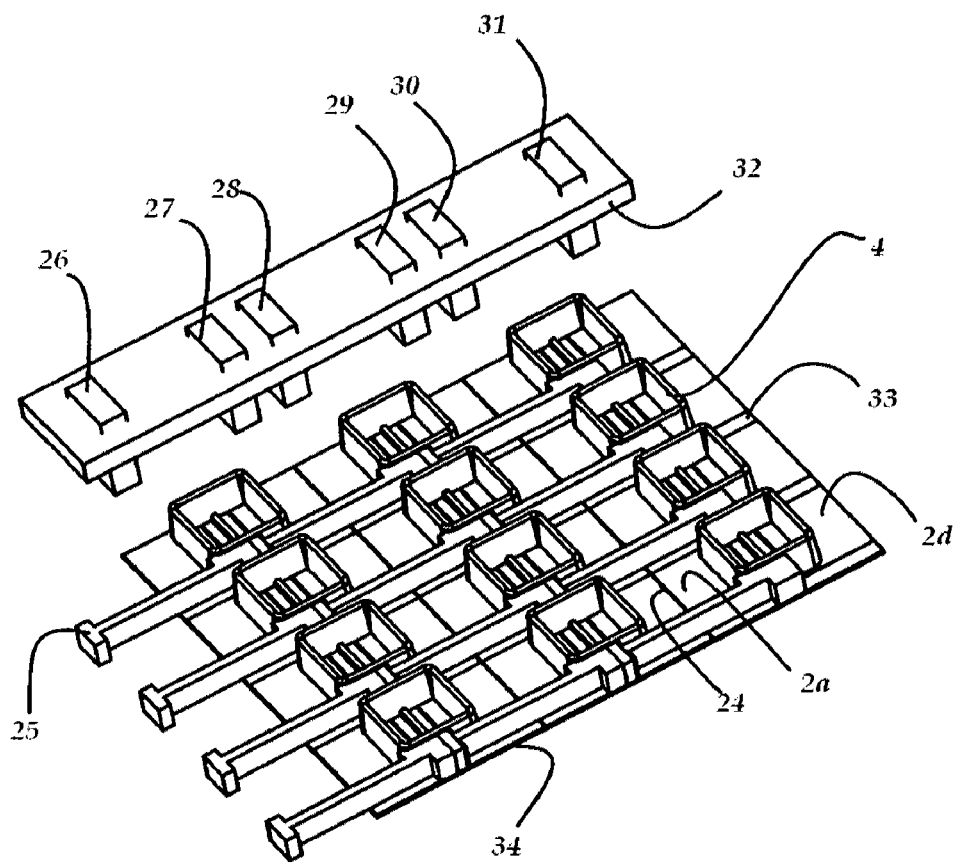
FIG. 10 shows a multi-well electroporation apparatus including an electrode plate and associated electrical contacts.

FIG. 10 shows an embodiment of the invention suitable for rapidly processing many samples by an operator or by a totally automated system. As an example, a sample 3×4 array is shown with 12 of the electroporation apparatus as described in any of the above embodiments, held together by multiple connecting strips 25. Alternatively, the array may be made on single substrate 34. For example, such a substrate, originally completely covered with conductive coating, may be etched so as to define the coated and uncoated regions of any of the previously described embodiments, as well as to remove the conductive coating from regions 24 and 33 in order to isolate the conductive coating around each well from the neighboring wells. This embodiment further comprises an electrical contact array 32, having pairs of electrical contacts 26 and 27, 28 and 29, 30 and 31, which is placed on the conductive surfaces 2a and 2d of a row of three separate electroporation wells. After application of the electric pulses, the electrical contact array 32 may be moved to the next row, and so on. Alternatively, the array size of the electrical contact array 32 may be the same as the array of wells, so as to provide the electroporation pulses to all wells without having to move the contact array 32. Those skilled in the art will recognize variations in the array that will provide for a variety of multiple chamber electroporation processes.

Figure 11:
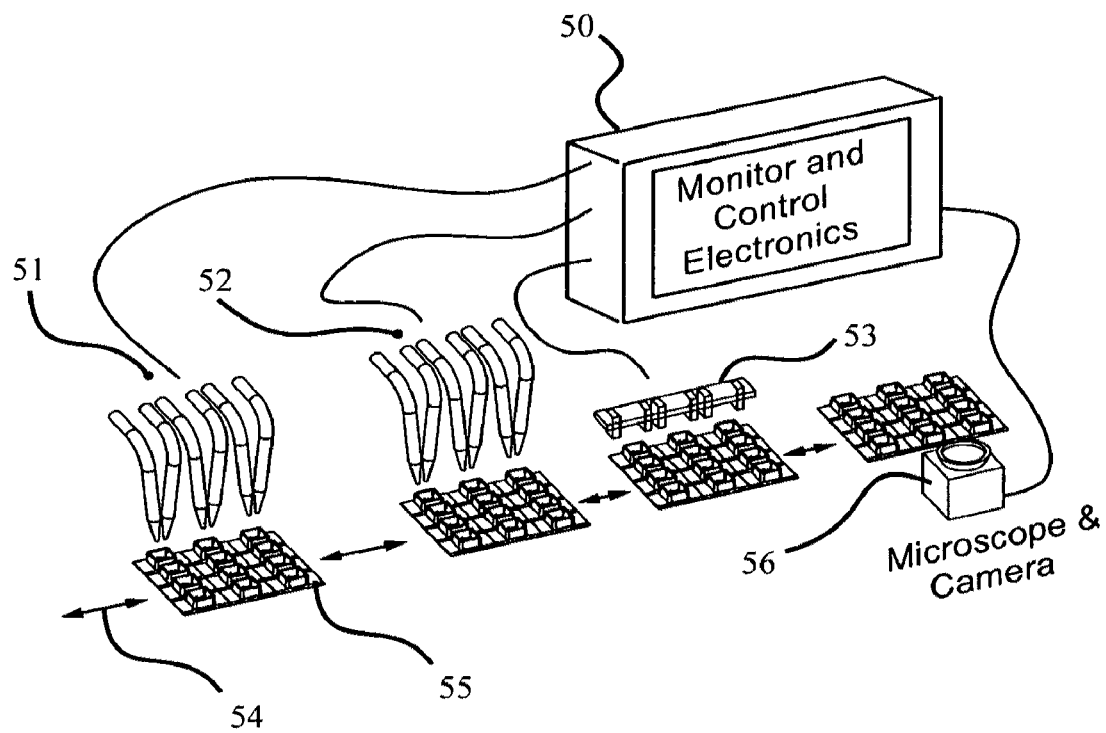
FIG. 11 shows a high throughput electroporation system that includes robotic fluid handling and automated image capture and analysis.

FIG. 11 shows an embodiment of the invention as an automated high throughput machine where any combination of fluid handling, electroporation pulse delivery, and subsequent image capture and analysis may be performed by robotic equipment. Such an arrangement allows for rapid processing of many cell samples with under a variety of electroporation settings. A computer 50 controls a conveyor mechanism 54 that transports multi-well electroporation plates 55 from an operator's station or an automated incubation centre. A fluid handling and dispensing machine 51 is used to seed cells and supply cell growth media under control of the computer 50. Cells may be returned to the incubator for later retrieval. The multi-well plate is moved along the conveyor to a position where electroporation buffer is introduced by another fluid handling system 52. From there, the multi-well plate is indexed to a station where a multipoint connection tool 53 is used to electroporate each well according to the control signals from the computer 50. Following electroporation, the multi-well plate may be attended by the fluid handler 52, or the cells in the various wells may be photographed by a digital camera 56 for subsequent manual or automated analysis.

Figure 13:
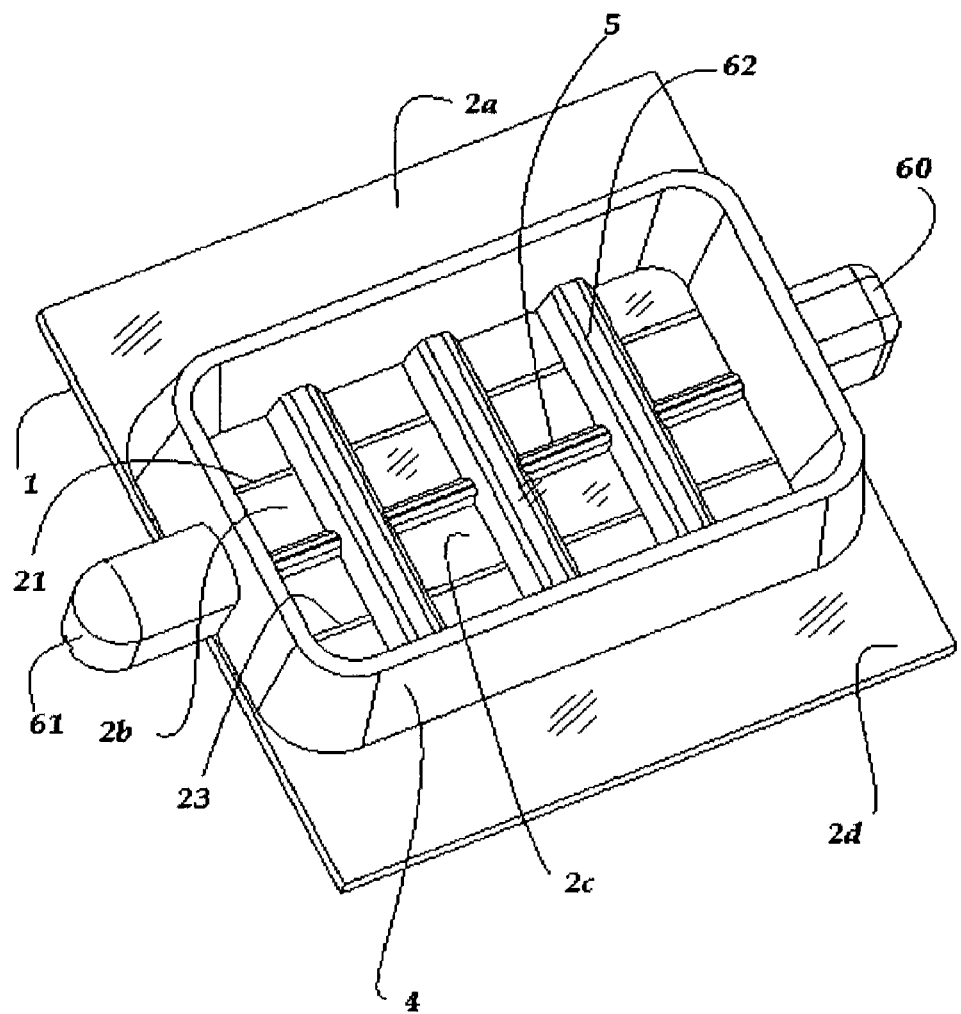
FIG. 13 shows another embodiment of a multi-well electroporation apparatus.

The embodiment shown in FIG. 13 is similar to that of FIG. 8, but has additional cross bars 62 that subdivide the area of the chamber into four regions. The cross bars 62 are higher than the barrier 5. With this arrangement it is possible to flood pairs of wells across the barrier 5 separately form other pairs; Therefore, it is possible to have different cells and/or different solutions in each of the pairs of wells created by the cross bars 62, during an electroporation experiment.

The multi-well embodiment may have a characteristic marking, shape, and/or configuration for orientation of the wells, which may be important when using different cells and/or solutions in the wells. For example, in the multi-well embodiment of FIG. 13, tabs 60 and 61 may have different shapes to help identify the wells and properly orient the chamber. These tabs may also provide easier handling of the chamber, with or without a lid, and they may aid in correctly locating the slide in the slide carrier for the electroporation process. In the latter case the slide carrier may have corresponding notches for receiving the tabs 60,61.

Figure 14:
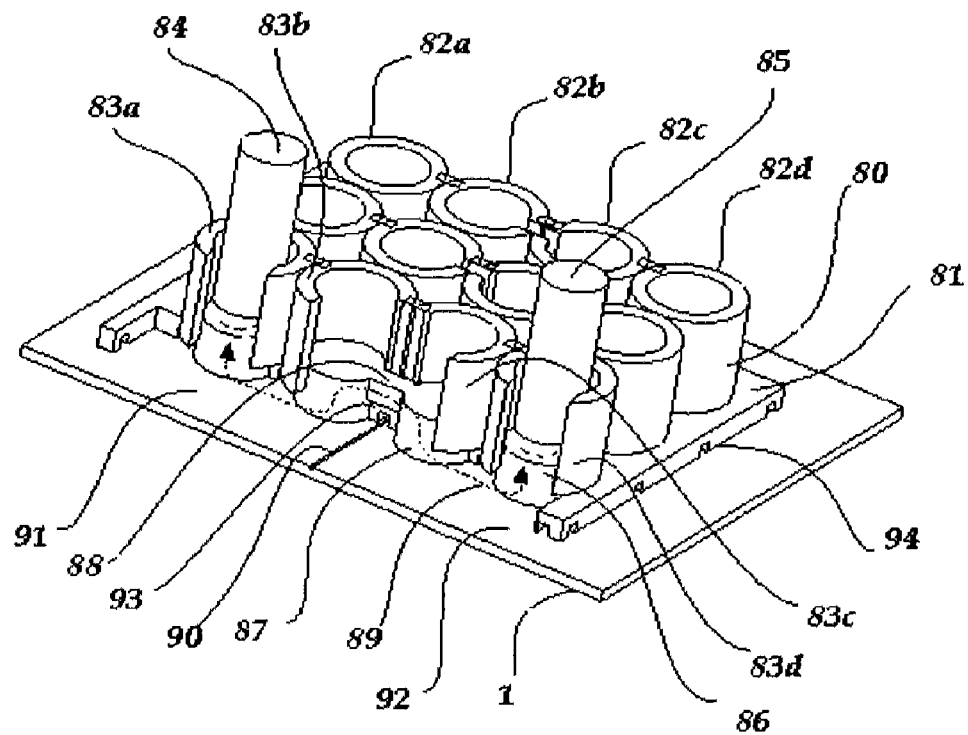
FIG. 14 shows another embodiment of a multi-well electroporation apparatus.

FIG. 14 shows a multi-well embodiment having an array of tubular wells 80. The spacing and height dimensions of the wells may conveniently be the same as those that are commonly used in the manufacture of 96-well tissue culture plates. The array has three sets of 4 well groups, each 4 well group in a linear arrangement. One such group is identified by reference numerals 82a, 82b, 82c, 82d. Another group of 4 wells is shown in cut-away view as 83a, 83b, 83c, 83d. The second and third wells of each 4 well group, e.g., wells 83b and 83c, are joined so as to share a common compartment. As in embodiments described above, a barrier 93 is provided at the bottom of the wells 83b and 83c, which separates the lower portion of the common compartment of wells 83b and 83c. When wells 83b and 83c are filled with growth medium/ conductive solution to a depth sufficient to overflow the barrier 93, the solution 88 may flow freely between wells 83b and 83c. Cells may be suspended in the growth medium in wells 83b and 83c and/or grown on the conductive glass surface.

The array of wells 80 and associated bottom plate 81 may be formed as a single plastic unit with holes in the wells passing through the bottom plate 81. This assembly may be bonded to the conductively coated surface of the glass slide 1, the bonds being made along grooves 94 in the lower side of the bottom plate 81. The grooves 94 pass between the wells such that once the bottom plate 81 is bonded to the glass, the solution in any well is isolated from the solution in every other well, except where there is an allowance for a solution bridge 88, such as between wells 83b and 83c.

The conductive glass surface is divided into two separate regions 91 and 92 by a thin line 90 lacking the conductive coating. The line 90 bisects all of the three of the 4 well groups shown in FIG. 14, passing beneath the barrier 93. Electrodes 84 and 85 fit into wells 83a and 83d respectively. The electrodes make contact with conductive portions of the substrate via any suitable electrical contact. For example, the electrodes may make contact with a conductive solution in those wells, which solution may or may not be the same as the solution in wells 83b and 83c. A source of electric potential, such as a pulse generator, delivers an electrical pulse through the electrodes 84 and 85 and the circuit is completed as the current follows a path from electrode 84, through the conductive solution in well 83a, to the conductive coating of region 91 of the substrate 1, to the bottom of well 83b, through cells growing thereon and/or through suspension cells and solution containing growth medium in well 83b, through the solution and over the barrier 93 to the well 83c, through the growth medium and suspension cells and/or adherent cells on the bottom of well 83c, through the conductive coating region 92 of the substrate 1, to the bottom of well 83d, through the conductive solution therein and up to the electrode 85. In one embodiment, the pulse generator may apply successive pulses of alternating polarity to electrodes 84 and 85.

A feature of this embodiment is that the electrodes 84 and 85 never come in direct contact with the growth medium in which the cells are being treated. This is suitable for automated electroporation systems wherein electrodes do not have to be replaced or cleaned between samples.

To maintain sterility and simplify handling, particularly while growing cells before and after electroporation, any of the embodiments of the electroporation chamber described herein may be provided with a lid.

The lid, which may be made from the same material as the electroporation device, and/or substantially optically transparent, may be provided with a securing mechanism such as one or more bumps or ridges that mate with corresponding features of the electroporation device, so as to hold the lid in place during handling. In one embodiment the securing mechanism may have a combination of a pinching tab at one end and a raised pivot point on the undersurface of the lid at the opposite end. With such an arrangement it is possible to lock the lid onto the chamber with one hand by simply pressing the pinching tab end down. The lid may be unlocked with one hand by applying pressure to the opposite end of the lid, which, owing to the raised pivot point, causes a slight tilting of the lid and lifts the pinching tabs away from the chamber. Numerous other arrangements and securing mechanisms will be readily apparent to those of ordinary skill in the art.

The lid may further include on its lower (inside) surface a series of bumps or ridges, to provide regions to which any trapped bubbles may escape.

A further benefit of a lid as described herein is that when it is desired to take pictures of the cells, before or after electroporation, buffer fluid can be used to fill the chamber to the top and the lid put in place to provide a flat, meniscus free surface that prevents visualization problems (i.e., distortion of the image) that may occur when looking through a curved fluid surface.

The contents of all cited publications are incorporated herein by reference in their entirety.

EQUIVALENTS

Those of ordinary skill in the art will recognize, or be able to ascertain through routine experimentation, equivalents to the embodiments described herein. Such embodiments are within the scope of the invention and are covered by the appended claims.

REFERENCES

Boccaccio, C., et al., Induction of epithelial tubules by growth factor HGF depends on the STAT pathway, Nature 391: 285-288, 1988.
Fick, J., et al., The extent of heterocellular communication mediated by gap junctions is predictive of bystander tumor cytotoxicity in vitro, PNAS USA, 92:11071-11075, 1995.
Khline et al., A Single Cell Electroporation Chip, The Royal Society of Chemistry, Lab Chip 5:38-43, 2005.
Raptis, L., et al., "Dissecting Pathways; in Situ Electroporation for the Study of Signal Transduction and Gap Junctional Communication", in Chapter 44, Cell Biology, a Handbook, Elsevier Science, Cambridge, 2005.
Yu-Cheng Lin et al., Electroporation microchips for in vitro gene transfection, J. Micromech. Microeng. 11:542-547, 2001.
Wood, K., et al., Electroactive controlled release films, PNAS 105:2280-2285, 2008.
Yaoita et al., Potential-Controlled Morphological Change and Lysis of HeLa Cells Cultured on an Electrode Surface, Biochemistry and Bioenergetics 20:169-177, 1988.

We claim:
1. An apparatus for electroporating cells, comprising:
(a) first and second substantially coplanar electrodes, wherein the first and second substantially coplanar electrodes each comprise an electrically-conductive coating disposed on a substrate and are positioned to create an electric field therebetween when connected to a source of electric potential;

(b) containment means disposed on at least a portion of the first and second electrodes, that contains the cells in solution; and (c) an electrically non-conductive barrier disposed between the first and second electrodes that divides the containment means into first and second portions and directs at least a portion of the electric field thereover.

2. The apparatus of claim 1, wherein the first electrode comprises a first substrate and an electrically-conductive coating thereon and the second electrode comprises a second substrate and an electrically-conductive coating thereon.

3. The apparatus of claim 1, wherein the first electrode comprises a first electrically-conductive coating disposed on a substrate and the second electrode comprises a second electrically-conductive coating disposed on the substrate.

4. The apparatus of claim 1, wherein the first and second electrodes are substantially optically transparent.

5. The apparatus of claim 1, wherein the barrier is of a height less than a height of the containment means.

6. The apparatus of claim 1, wherein the barrier divides the containment means into two portions and prevents transfer of cells between the two portions.

7. The apparatus of claim 2, wherein the electrically-conductive coating comprises at least one of indium tin oxide (ITO), gold, doped indium oxide, cadmium oxide, cadmium stannate, zinc oxide, zinc cadmium sulfite or titanium nitride, antimony oxide, aluminum oxide, titanium oxide, copper indium oxide, and carbon nanotubes.

8. The apparatus of claim 2, wherein the electrically-conductive coating comprises indium tin oxide (ITO).

9. The apparatus of claim 1, wherein at least one of the first and second portions of the containment means includes at least one electrically non-conductive region adjacent to and substantially coplanar with the first or second electrode.

10. The apparatus of claim 1, wherein the solution is an electrolyte and includes material to be introduced into at least a portion of the cells.

11. The apparatus of claim 10, wherein the material is selected from proteins, peptides, nucleic acids (DNA, RNA, siRNA), compounds such as dyes, quantum dots, nanoparticles, carbon nanotubes, fluorescent markers, drugs, small molecules, viruses, and phages, and combinations and/or fragments thereof.

12. The apparatus of claim 1, wherein the first and second electrodes comprise a microscope slide.

13. The apparatus of claim 1, further comprising an electrically conductive barrier disposed on top of the electrically non-conductive barrier.

14. The apparatus of claim 1, wherein the first and/or the second coplanar electrode comprises one or more electrically isolated region.

15. An apparatus for electroporating cells comprising a plurality of the electroporation apparatus of claim 1 as an array.

16. The apparatus of claim 15, having at least one automated function selected from fluid handling, electroporation pulse delivery, image capture, and image analysis.

17. A method for electroporating cells, comprising:

(a) maintaining the cells in a solution on or above first and second substantially coplanar electrodes separated by an electrically non-conductive barrier, wherein the first and second substantially coplanar electrodes each comprise an electrically-conductive coating disposed on a substrate, the first and second electrodes positioned to create an electric field therebetween when connected to a source of electric potential, the solution covering the electrically non-conductive barrier and comprising an electrolyte and material to be introduced into the cells; and (b) applying an electric potential to the first and second electrodes;

wherein an electric field resulting from the electric potential is established over the electrically non-conductive barrier between the first and second electrodes; and wherein the electric field causes electroporation of at least a portion of the cells.

18. The method of claim 17, wherein maintaining cells comprises maintaining adherent cells and/or suspended cells.

19. The method of claim 17, wherein maintaining the cells additionally comprises maintaining the cells on or above a non-conductive region of a substrate that is adjacent to and substantially coplanar with at least one of the first and second electrodes;

wherein the electric field causes electroporation of cells on or above a said first or second electrode and does not cause electroporation of cells on or above a said non-conducting region, such that regions of electroporated and non-electroporated cells are established about a line corresponding to a juncture of a non-conducting region and an electrode.

20. The method of claim 17, wherein electroporating cells comprises introducing into at least a portion of the cells a material selected from proteins, peptides, nucleic acids (DNA, RNA, siRNA), compounds such as dyes, quantum dots, nanoparticles, carbon nanotubes, fluorescent markers, drugs, small molecules, viruses, and phages, and combinations and/or fragments thereof.

21. The method of claim 17, further comprising:

disposing an electrically conductive barrier on the electrically non-conductive barrier, the solution covering the electrically non-conductive barrier and contacting the electrically conductive barrier;

wherein the electric field is established over the electrically non-conductive barrier and through the electrically conductive barrier.

22. The method of claim 17, further comprising:

providing one or more electrically isolated region within the first and/or the second coplanar electrode;

wherein cells associated with the one or more electrically isolated region are substantially not electroporated.

23. A method for assessing gap junctions in cells, comprising:

subjecting cells to the method of claim 22; and monitoring transfer of material from electroporated cells to cells not electroporated;

wherein said transfer of material is indicative of gap junctions between cells.

* * * * *